United States Patent [19]

Mason, Jr. et al.

[11] Patent Number: 4,706,600
[45] Date of Patent: Nov. 17, 1987

[54] KIT FOR MAKING SETS OF TRANSPARENT FINGERPRINTS USING DIFFERENTIAL ADHESION

[75] Inventors: Stanley I. Mason, Jr., Weston; Allan P. Wolfe, Redding; Robert B. Turner, Weston, all of Conn.

[73] Assignee: Crisis Communication, Inc., Weston, Conn.

[21] Appl. No.: 928,966

[22] Filed: Nov. 10, 1986

[51] Int. Cl.$^4$ ............................................... B41K 1/00
[52] U.S. Cl. ........................................ 118/31.5; 427/1
[58] Field of Search .......................... 118/31.5; 427/1; 428/40, 212

[56] References Cited

U.S. PATENT DOCUMENTS

| 3,467,055 | 9/1969 | Yonchar | 118/31.5 |
| 3,664,910 | 5/1972 | Hollie | 118/31.5 |
| 4,574,098 | 3/1986 | Sampson | 428/212 |

FOREIGN PATENT DOCUMENTS 2063710  6/1981  United Kingdom .................. 428/40

Primary Examiner—John E. Kittle
Assistant Examiner—Terry J. Owens
Attorney, Agent, or Firm—Haynes N. Johnson

[57] ABSTRACT

A kit for making permanently sealed transparent fingerprints using differential adhesion, including dry ink and means for applying the ink to fingers, a transfer strip having a backing sheet, a transparent adhesive print strip, and a protective cover, a transparent record sheet, print adhesive adhering together the protective cover and the adhesive print strip, backing adhesive adhering together backing sheet and the adhesive print strip, and the adhesives having such differential adhesion as to cause greater adhesion between the adhesive print strip and the backing sheet than between the adhesive print strip and the protective cover, and greater adhesion between the adhesive print strip and the record sheet than between the adhesive print strip and the backing sheet.

7 Claims, 11 Drawing Figures

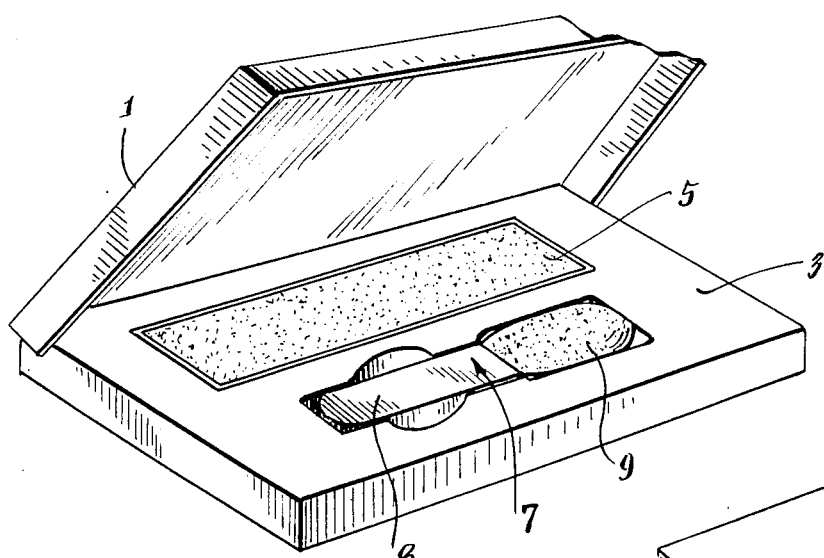
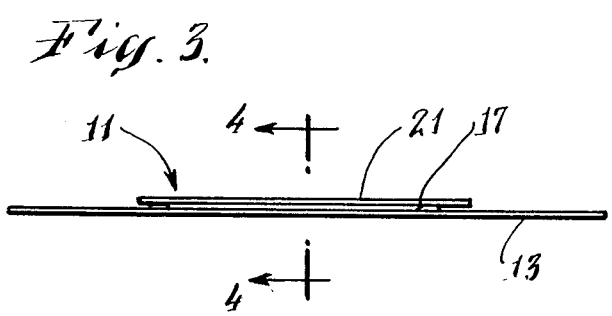
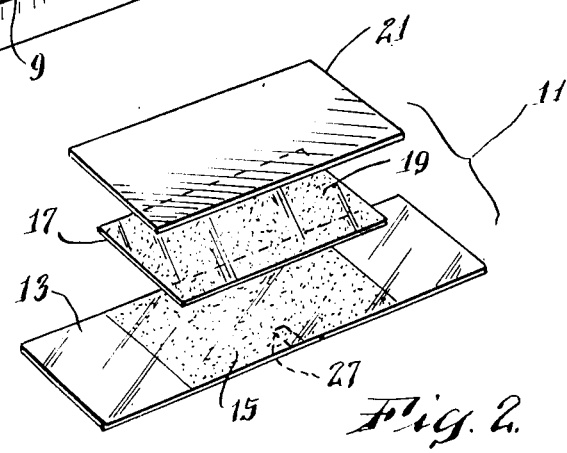
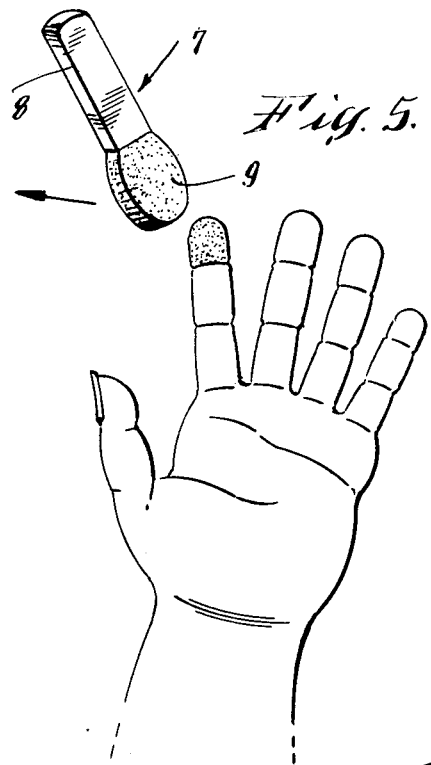
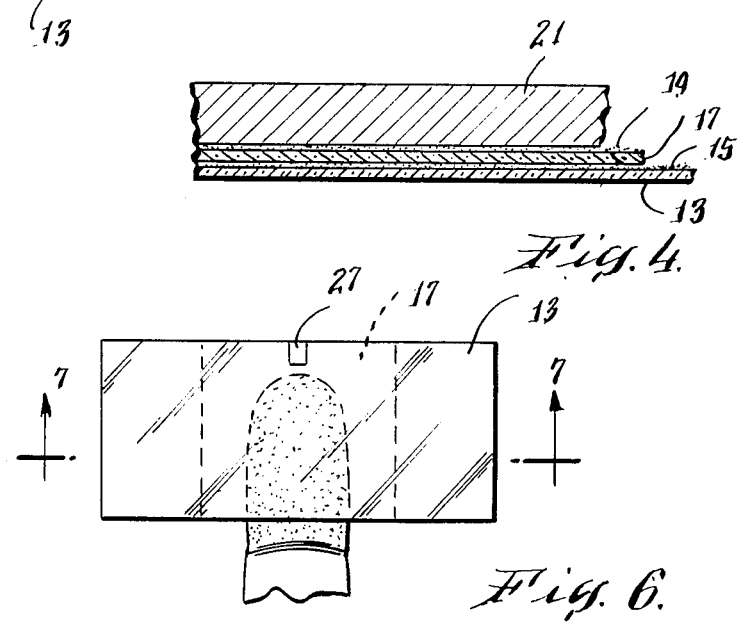
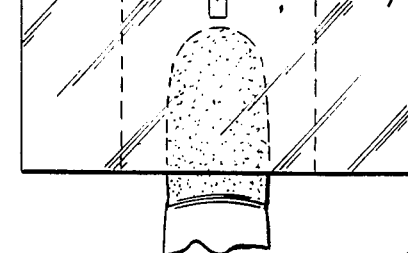
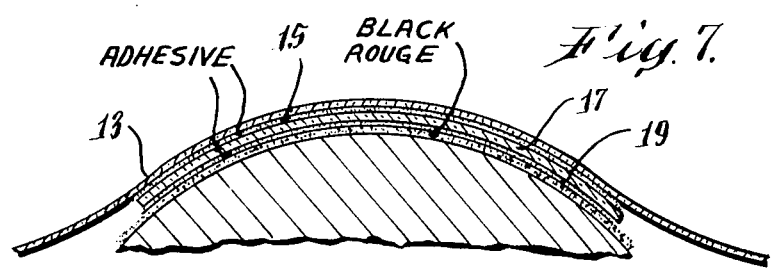

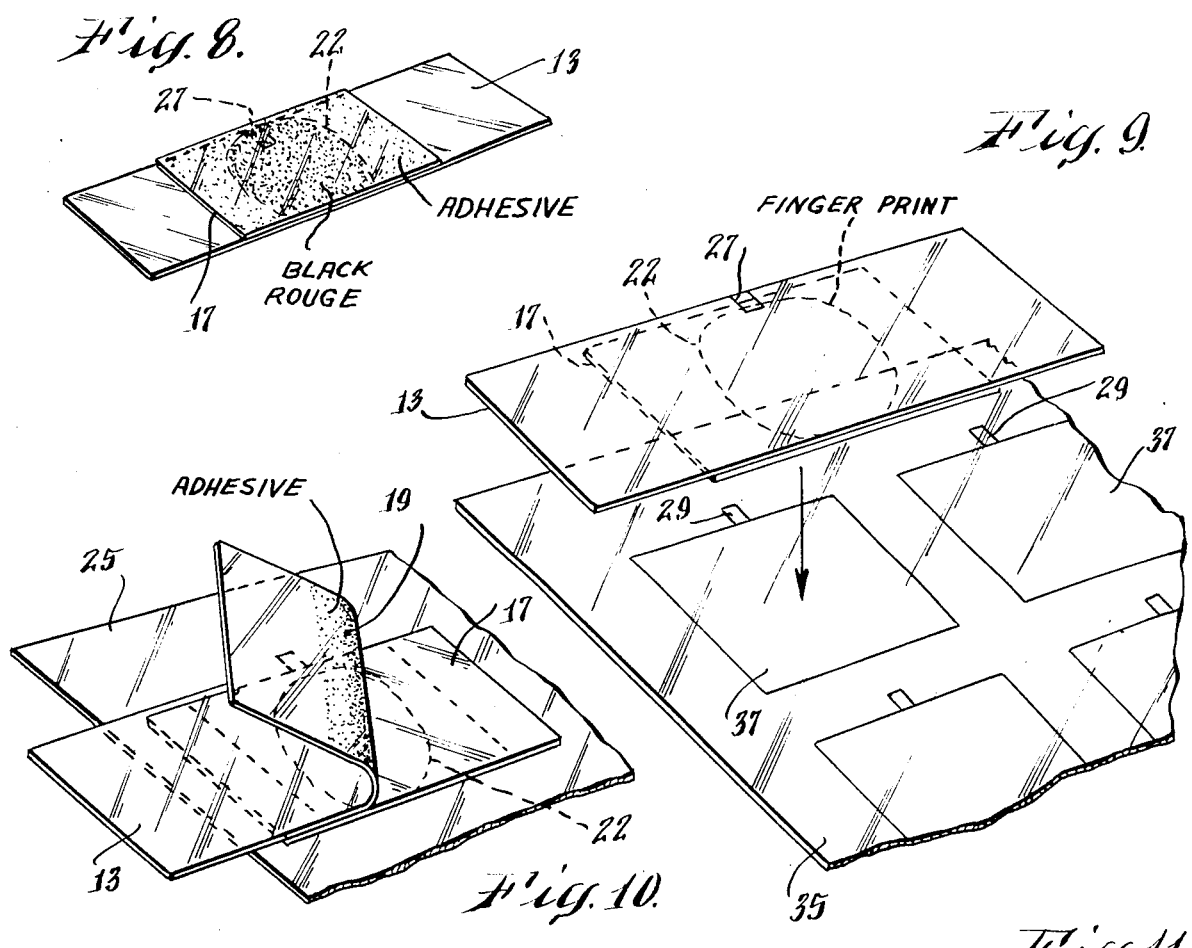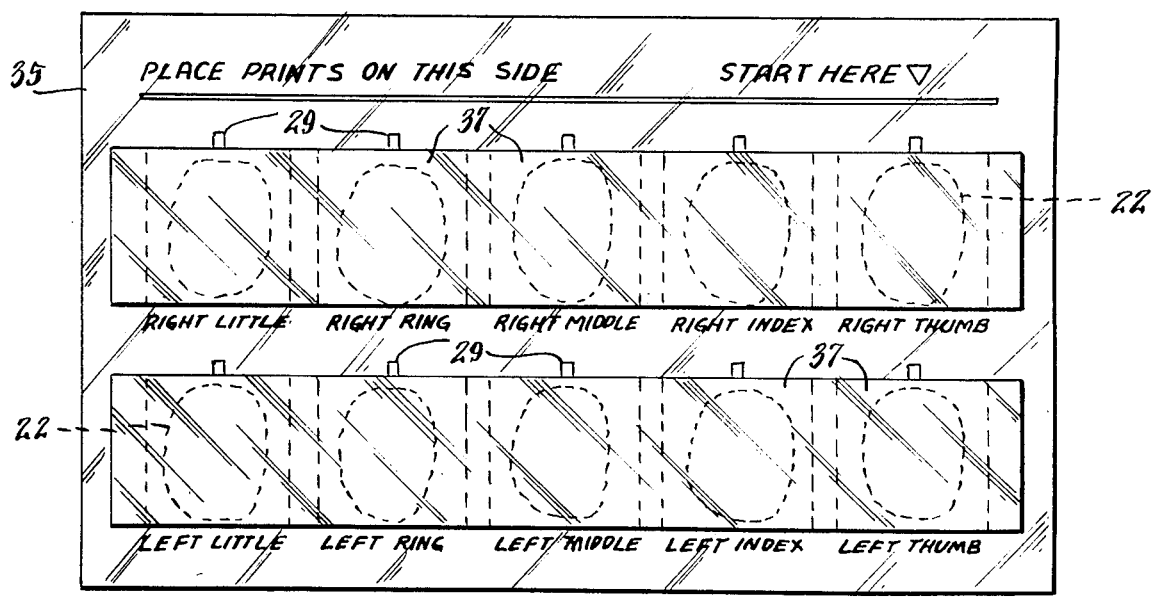

KIT FOR MAKING SETS OF TRANSPARENT FINGERPRINTS USING DIFFERENTIAL ADHESION

FIELD OF THE INVENTION

This invention relates to the field of dry fingerprinting, in particular, to fingerprints that may be produced and mounted in a sealed, transparent sandwich so that they can be seen in a non-reversed position and can be projected.

The system is a dry process and, as such, particularly useful when taking children's fingerprints.

BRIEF SUMMARY OF THE INVENTION

A kit is provided enabling fingerprints to be made, especially those of small children, without the use of wet ink. The prints are sandwiched between two sheets of clear plastic so that they may readily be viewed or projected, and are protected against accidental smearing or erasure.

The kit includes dry ink to be applied to the fingers, a dauber for the ink, transfer strips for receiving the inked prints and saving them on a transparent record sheet, using the principle of differential adhesion.

The transfer strips include a backing sheet with an adhesive print strip adhered to it and a protective cover. The print strip is made of transparent plastic sheet and has transparent adhesive on both sides. The adhesive adheres it to the backing sheet and to the protective cover.

In use, the protective cover is removed, exposing the adhesive print strip and the finger, previously inked, is pressed against it. The print side of the print strip is pressed against another sheet of clear plastic, the record sheet; and the strip, due to differential adhesion, adheres to the record sheet and leaves the backing sheet. The result is a sandwich formed of two sheets of clear plastic adhered together with the fingerprint in between. The print is thereby permanently protected by the sheets, and may be viewed from either side or projected.

Preferably the record sheet has spaces on it for prints of all ten fingers, and will have indexing marks corresponding to similar marks on the adhesive print strip for use in alignment of the prints when they are being mounted.

Prior fingerprinting systems have normally used a wet or viscous ink and have produced a reversed image. The present system produces a print in a protective transparent sandwich which may be viewed from either side or projected. The only known prior dry ink system known to the inventors is for post mortem prints. It does not utilize differential adhesion, nor does it produce a transparent print.

DESCRIPTION OF THE DRAWINGS

Turning to the drawings:

FIG. 1 is a perspective view of the fingerprint kit of our invention.

FIG. 2 is an exploded view of a transfer strip.

FIG. 3 is a side elevation of a transfer strip.

FIG. 4 is an enlarged section, taken on line 4—4 of FIG. 3, showing the backing sheet, the adhesive print strip, and the protective cover, with adhesive layers between them.

FIG. 5 is a perspective view of a child's hand as dry ink is being applied with a dauber.

FIG. 6 is a view through the adhesive print strip and the backing sheet of the fingerprint being applied to the adhesive print strip.

FIG. 7 is a section, taken on line 7—7 of FIG. 6, showing the print being taken from the child's finger.

FIG. 8 is a perspective view of the adhesive print strip and backing sheet with the newly-taken fingerprint on it.

FIG. 9 is a perspective view showing the application of the print to the record sheet to form a sandwich with the print in between two sheets of clear plastic. It shows the use of the alignment marks.

FIG. 10 is a perspective view showing the removal of the backing sheet from the sandwich.

FIG. 11 shows a record sheet bearing a complete set of finished prints.

DETAILED DESCRIPTION OF THE INVENTION

The kit of our invention includes a supply of dry ink and a dauber with which to apply it, transfer strips to receive the fingerprint, and transparent record sheets to receive the prints from the transfer strips and to form a permanent protective package.

The kit comes in a kit box 1 which has a face plate 3 with recesses to receive an exposed container of dry ink 5 and to hold a dauber 7. The transfer strips 11 and the record sheet 25 are normally packaged outside the kit box 1.

Dauber 7 includes a handle 8 and a foam portion 9. In use, the foam portion is rubbed across the dry ink and then rubbed across the finger, to apply the ink.

Transfer strip 11 is formed of a backing sheet 13, an adhesive print strip 17 and a protective cover 21. These are adhered together by adhesives, described below, which have the important characteristic of differential adhesion. That is, the adherence of backing sheet 13 to print strip 17 is greater than that of protective cover 21 to print strip 17 and backing sheet 13; the adherence of print strip 19 to backing sheet 13 is greater than the adherence of adhesive print strip 17 to a finger coated with dry ink (though the dry ink should stick to print strip 19 and leave the finger); and the adherence of print strip 17 to backing sheet 15 is less than the adherence of strip 17 to record sheet 25.

In essence, the above discussion of adherence says that (1) the protective cover can be peeled from the print strip 17 and backing sheet 13 without separating strip 19 from sheet 13; (2) a print can be taken from the finger and have the backing sheet 13 continue to adhere to the adhesive print strip 15; and (3) the print strip 17 will adhere to record sheet 25 and so peel from backing sheet 13 to make the sandwich.

As mentioned above, FIG. 2 is an exploded view of a transfer strip 11. This is shown in section in FIGS. 3 and 4. Strip 11 includes backing sheet 13, adhered to adhesive print strip 17 by backing adhesive 15, and protective cover 21 adhered to adhesive print strip 17 by print adhesive 19. Under some circumstances, protective cover can be dispensed with.

Backing sheet 13 is made of 280 gauge clear PVC. Other polymer sheets, such as polypropylene or polyethylene may be used, as long as they do not stretch appreciably. Adhesive print strip 17 is made of a clear plastic, preferably 2 mil biaxially-oriented polypropylene. Protective cover 21 is a 40 to 90 lb. paper, silicone release coated. Record sheet 25 is a is a transparent 5 mil polypropylene or PVC.

Backing adhesive 15 is between backing sheet 13 and print strip 17. It is a pressure sensitive acrylic solvent-based adhesive, preferably about 0.1 to about 1 mil thick, having a 180° peel strength of about 8 oz./in. In addition, the side of print strip 17 facing the backing sheet 13 is best coated with a silicone-based release agent having a 180° peel strength of 15 to 20 oz./in.

Print adhesive 19 is a 0.2 mil thick layer of solvent-based acrylic adhesive with a 180° peel strength of about 3 oz./in.

By using solvent-based adhesives, the final record fingerprint and its sandwich will dry.

It will be noted that the peel strengths of the adhesives serve to satisfy the criteria given above for differential adhesion. Naturally, others could also be chosen that would satisfy the given criteria. Likewise, other sheet materials could be used as long as they satisfied the necessary criteria.

The dry ink 5 which is used is in the form of a dry adherent paste, somewhat like black rouge or eyeshadow. One formulation, in descending order of predominance, is formed of talc (about 75 to 90%), zinc stearate (10 to 15%), isopropyl palmitate (5 to 10%), and lanolin oil (2 to 5%), with concentrations of less than 1% of methylparaben, imidazolidinyl urea, propylparaben, and BHA.

In use, the dauber 7 is coated with dry ink 5 and the ink applied to a child's fingers (FIG. 5). Protective cover 21 is removed from transfer strip 11, exposing the adhesive surface 19 of adhesive print strip 17. (Due to the differential adhesion, strip 17 remains adhered to backing sheet 13 when cover 21 is removed). The adhesive surface of print strip 17 is then pressed against the finger, and the dry ink adheres to the strip producing a print 22 on the surface of adhesive strip 17 (FIG. 8).

The fingerprint side of print strip 17 and backing sheet 13 is then pressed against record sheet 25. (If desired, the backing sheet 13 can be made with a printed alignment mark 27, with a similar mark 29 on record sheet 25, to permit alignment). Backing sheet 13 is then peeled off leaving the print strip 19 adhering to the record sheet 25 (FIG. 10).

Due to the differential adhesion discussed above, the adherence of adhesive print strip 17 to record sheet 25 will be greater than the strip's adherence to backing sheet 13; consequently, backing sheet 13 can be peeled off leaving strip adhered to record sheet 25. This will result in a sandwich formed of record sheet 25 and print strip 17, with the fingerprint itself sealed between the two. Since solvent-based adhesives have been used, the adhesives will dry, leaving a sealed permanent print.

Strip 17 and sheet 25 are transparent. As a result, the fingerprint can be viewed from either side (direct or reversed) or it can be projected.

In order to have a full set of fingerprints, it is useful to have a print card 35 with spaces for the print of each finger. (FIGS. 9 and 11). The spaces are formed of ten openings 37 in the card, the openings being backed by record sheet 25. Here sheet 25 may be a single sheet that passes behind each of the openings and is adhered to the back of card 35. As stated above, there may be alignment marks 29 proximate to openings 37 for use with similar marks 27 on record sheet to position the prints when securing print strip 1 to record sheet 25.

We claim:

1. A kit for making permanently sealed transparent fingerprints using differential adhesion, said kit including
    dry ink and means for applying same to fingers,
    a transfer strip having a backing sheet, a transparent adhesive print strip, and a protective cover,
    a transparent record sheet,
    print adhesive adhering together said protective cover and said adhesive print strip,
    backing adhesive adhering together said backing sheet and said adhesive print strip, and
    said adhesives having such differential adhesion as to cause greater adhesion between said adhesive print strip and said backing sheet than between said adhesive print strip and said protective cover, and greater adhesion between said adhesive print strip and said record sheet than between said adhesive print strip and said backing sheet,
    whereby dry ink fingerprints can be applied to said adhesive print strip and said adhesive print strip can be adhered to said record sheet to sandwich said fingerprint between said adhesive print strip and said record sheet.

2. A kit for making permanently sealed transparent fingerprints as set forth in claim 1 in which said backing sheet and said record sheet include alignment marks, whereby said sheets may be aligned when being adhered together.

3. A kit for making permanently sealed transparent fingerprints as set forth in claim 1 in which said record sheet includes spaces for ten fingerprints.

4. A kit for making permanently sealed transparent fingerprints as set forth in claim 3 including a print card having fingerprint openings therein affixed to said record sheet.

5. A kit for making permanently sealed transparent fingerprints using differential adhesion, said kit including
    a backing sheet and a transparent adhesive print strip,
    a transparent record sheet,
    backing adhesive adhering together said backing sheet and said adhesive print strip, and
    said adhesives having such differential adhesion as to cause greater adhesion between said adhesive print strip and said record sheet than between said adhesive print strip and said backing sheet,
    whereby dry ink fingerprints can be applied to said adhesive print strip and said adhesive print strip can be adhered to said record sheet to sandwich said fingerprint between said adhesive print strip and said record sheet.

6. A kit for making permanently sealed transparent fingerprints as set forth in claim 5 including a protective cover sheet removably adhered to said adhesive print strip.

7. A transfer strip for use in making permanently sealed transparent fingerprints on a transparent record sheet using differential adhesion, said transfer strip including
    a backing sheet, a transparent adhesive print strip to receive a fingerprint, and a protective cover,
    print adhesive adhering together said protective cover and said adhesive print strip,
    backing adhesive adhering together said backing sheet and said adhesive print strip, and
    said adhesives having such differential adhesion as to cause greater adhesion between said adhesive print strip and said backing sheet than between said adhesive print strip and said protective cover, and greater adhesion between said adhesive print strip and said record sheet than between said adhesive print strip and said backing sheet,
    whereby dry ink fingerprints can be applied to said adhesive print strip and said adhesive print strip can be adhered to said record sheet to sandwich said fingerprint between said adhesive print strip and said record sheet.

* * * * *